US007450725B2

(12) United States Patent
Vaishya

(10) Patent No.: US 7,450,725 B2
(45) Date of Patent: Nov. 11, 2008

(54) DIGITAL FILTER MODELING FOR ACTIVE NOISE CANCELLATION

(75) Inventor: Manish Vaishya, Auburn Hills, MI (US)

(73) Assignee: Mahle International GmbH, Stuttgart (DE)

( * ) Notice: Subject to any disclaimer, the term of this patent is extended or adjusted under 35 U.S.C. 154(b) by 1446 days.

(21) Appl. No.: 10/315,849

(22) Filed: Dec. 9, 2002

(65) Prior Publication Data

US 2003/0112980 A1 Jun. 19, 2003

Related U.S. Application Data

(60) Provisional application No. 60/341,586, filed on Dec. 17, 2001.

(51) Int. Cl.
*A61F 11/06* (2006.01)
*G10K 11/16* (2006.01)
*H03B 29/00* (2006.01)

(52) U.S. Cl. .................................... 381/71.1; 381/71.9

(58) Field of Classification Search ..... 381/71.1–71.14; 708/322
See application file for complete search history.

(56) References Cited

U.S. PATENT DOCUMENTS 5,381,485 A * 1/1995 Elliott ....................... 381/71.6
5,553,153 A * 9/1996 Eatwell ................... 381/71.12
5,668,747 A * 9/1997 Ohashi ....................... 708/322
5,689,572 A 11/1997 Ohki et al.
6,208,949 B1 * 3/2001 Eatwell ...................... 702/189
6,275,592 B1 * 8/2001 Vartiainen ................ 381/71.11
6,594,365 B1 * 7/2003 Eatwell ..................... 381/73.1

FOREIGN PATENT DOCUMENTS

GB 2 069 280 A 8/1981
GB 2 203 016 A 10/1988
GB 2 287 851 A 9/1995
WO WO 94/24662 10/1994

OTHER PUBLICATIONS

Patents Act 1977: Search Report under Section 17 Date of Search: Mar. 27, 2003.

* cited by examiner

*Primary Examiner*—Xu Mei
(74) *Attorney, Agent, or Firm*—Carlson, Gaskey & Olds

(57) ABSTRACT

An active noise cancellation system (20) includes digital modeling of the physical path that is compensated for using a digital filter (34). An initial estimate of the time domain response of the system (20) is achieved using inverse time domain convolution to determine the signal values of a speaker (24) and a microphone (26) in the system. The estimated time domain response of the system is used to determine the initial estimate of the modeled digital filter. In one example, the initial estimate is then used as part of a convergence technique, such as a least mean squares algorithm. In another example, a plurality of initial estimates are determined and then averaged to arrive at the filter value used during noise cancellation.

7 Claims, 1 Drawing Sheet

DIGITAL FILTER MODELING FOR ACTIVE NOISE CANCELLATION

CROSS REFERENCE TO RELATED APPLICATIONS

This application claims priority to U.S. Provisional Application No. 60/341,586, which was filed on Dec. 17, 2001.

TECHNICAL FIELD

This invention generally relates to active noise cancellation systems. More particularly, this invention relates to digital filter modeling for use in a noise cancellation system.

DESCRIPTION OF THE PRIOR ART

Noise cancellation systems have a variety of uses. One example use is on automotive vehicles for reducing noise propagation into the passenger compartment.

Modern day vehicles typically include an air induction system. One drawback of air induction systems is that engine noise frequently travels through the air induction system and emanates out of the mouth of the air intake such that the noises are noticeable in the passenger compartment. This is particularly true under wide open throttle conditions. Various efforts have been made to reduce the amount of engine noise traveling through the air induction system. Some arrangements include using passive devices such as expansion chambers and Helmholtz resonators. Other efforts include active methods such as anti-noise generators.

Other sources of noise may be associated with a vehicle exhaust or a supercharger, for example. Regardless of the particular application, various challenges exist when designing an effective and economical noise cancellation system.

Typical active systems include a speaker that generates a sound to attenuate the noise. The sound from the speaker typically is out of phase with the noise and combines with the noise such that the result is a reduced noise, which results in less noise transmission into the passenger compartment, for example. The speaker sound can be referred to as a noise cancellation signal.

Digital signal processors such as microprocessors typically generate cancellation signals for driving the speaker to achieve the noise cancellation. The microprocessor typically requires some input from the relevant environment to adequately address the need for noise cancellation. In some examples, computer modeling is used so that the microprocessor is able to provide a desired level of noise cancellation.

While such systems are useful, they do not address all difficulties associated with operating an effective noise cancellation system. For example, such systems often rely upon a filtered-X least mean squares algorithm for modeling the error path in a feed forward control manner. White noise is generated and the response of the physical system is matched with the digital response of a modeled finite impulse response filter. Conventionally, the filter model begins at zero and is updated based upon the error signal using convergence techniques. The rate of convergence is limited by the white noise signal strength and depends upon the number of filter taps. Very long modeling times typically are required and, in many situations, the level of noise required produces an objectionable sound discernible by an individual in or near the vehicle.

There is a need for an improved technique for modeling a digital filter in a noise cancellation system that reduces the time required to obtain the filter values and reduces the audible noise level.

This invention provides an enhancement to active noise cancellation that reduces the time required to develop a filter model and reduces the level of noise required to calibrate the system.

SUMMARY OF THE INVENTION

In general terms, this invention is a method of modeling a digital filter for use in a noise cancellation system.

One method designed according to this invention includes determining a digital filter value for use in an active noise cancellation system by estimating an initial filter value based upon a time domain response of the system to a test signal. The filter eventually used during noise cancellation is determined using the estimated initial filter value.

In one example, the initial filter value is estimated by determining a time domain response of the system to the test signal using an inverse time domain convolution to obtain at least a portion of the time domain response. The initial filter value is estimated based upon the time domain response of the system. The inverse time domain convolution includes back-calculating coefficients of the filter from speaker and microphone signals from a convolution equation that describes the filter operation.

In one example implementation, a plurality of initial filter values are estimated. An average filter value based upon the plurality of estimated initial values then is used in one example as the initial estimated filter value for determining the filter value. In another example, the average estimated initial filter value may be used as the actual filter value during noise cancellation.

The various features and advantages of this invention will become apparent to those skilled in the art from the following detailed description of the currently preferred embodiments. The drawings that accompany the detailed description can be briefly described as follows.

DETAILED DESCRIPTION OF THE PREFERRED EMBODIMENT

Figure 1:
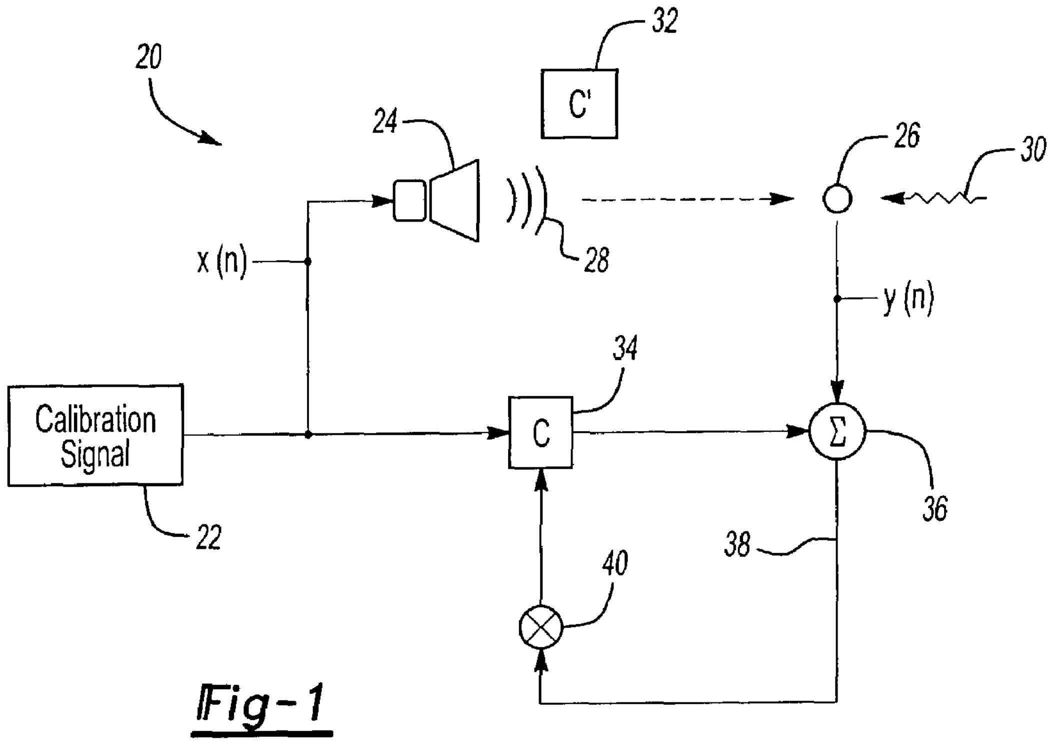
FIG. 1 schematically illustrates selected portions of an active noise cancellation system that employs a method designed according to this invention.

FIG. 1 schematically illustrates selected portions of a noise cancellation system 20. A signal generator 22 drives a speaker 24 to generate a noise corresponding to the signal provided to the speaker 24. A microphone 26 detects a combination of a sound 28 emanating from the speaker 24 and noise 30 associated with or within the structure where the noise cancellation system is applied. During a noise cancellation procedure, the sound 28 from the speaker 24 may be referred to as the noise cancellation signal within the system that effectively cancels out the noise 30 to provide the desired level of noise cancellation.

The speaker 24 may also be used to generate sounds 28 within the system that create noise for modeling the response of the system, for example. A modeling module 32 provides a software model (i.e., C-model) of the response of the portion of the system that includes the speaker 24 and the microphone 26 (i.e., the so-called secondary path). In the illustrated example, the modeling module 32 provides information regarding the effectiveness of a digital filter 34 and modifies the digital filter 34 to achieve a desired system operation.

In one example, the digital filter 34 is a finite impulse response (FIR) filter. The characteristics of such filters and the techniques for modeling them are generally known. Those skilled in the art who have the benefit of this description will be able to develop the necessary software to achieve the digital filter required to meet the needs of their particular situation.

This invention includes modeling the digital filter 34 using an initial estimate of the filter that is obtained by determining a time domain response of the system to a test noise signal.

In the illustrated example, the same signal from the signal generator 22 is provided to the speaker 24 and the initial estimate of the filter 34. The signal from the microphone 26 is combined with the signal from the filter 34 using a summer 36. The resulting error signal at 38 is then provided to a convergence module 40 for updating the values of the filter 34. This process is repeated until the filter value converges to that necessary to achieve the desired level of noise cancellation within the system. Those skilled in the art who have the benefit of this description will realize that a variety of convergence techniques may be used as known to accomplish the results needed for this portion of a noise cancellation system designed according to this invention.

In conventional systems, a least mean squares algorithm is applied to estimate the error path. A white noise is generated by a speaker that is then measured at the microphone. Simultaneously, the same signal is passed through the modeled digital filter over a certain duration or the number of taps in the filter. The difference between the filtered signal and the signal from the microphone is used to update the filter taps. As the error or difference between the signals is driven to zero, the filter converges to the correct value. With conventional approaches, the model for the digital filter is initialized at zero, primarily to avoid any bias during the adaptation process. A shortcoming of this approach, however, is that the convergence process may be slow and requires relatively long durations for modeling. Increasing the convergence rate typically causes too much scatter so that it is not possible to achieve an accurate model. The other alternative previously suggested is increasing the sound amplitude of the test noise signal, which is not desirable because it increases the level of undesirable sound heard by an individual.

This invention provides a faster convergence to the desired filter value using a low amplitude test noise signal. According to this invention, the digital model transfer function is computed directly to provide an initial estimate of the filter 34 by observing the input and output signals (i.e., the filtered signal and the microphone signal). This invention eliminates dependence upon adaptation and provides a very fast initial estimate. In one example, the duration of the initial estimate computation is on the order of the length of the filter 34. For example, a 62 tap filter at a 2 kiloHertz sampling frequency requires approximately 100 milliseconds for a sufficient number of averages to be computed to provide the estimated filter. Subsequently, the estimated model may be refined using other techniques, such as the least mean squares algorithm or multiple initial estimates may be determined and then averaged using a suitable averaging technique.

A time-domain method of this invention involves the inverse of the convolution integral that describes the digital filter. Accordingly, this invention provides a superior method compared to conventional Fourier methods, like the FFT, which work in the frequency domain. Eventually, the digital filter is implemented in the time domain and, therefore, a Fourier method requires utilizing an inverse FFT, which increases the amount of computation required and increases the time required to appropriately model the digital filter. This invention includes a mathematical technique that directly gives the time domain impulse response of the filter. In one example, this is achieved by inverting the matrix associated with the convolution process.

In one example, the initial estimate of the model for the filter 34 is made based upon direct measurement of the output and input signals of the error path 38. Assuming the speaker signals are represented by x(n) and the microphone signals are represented by y(n), then the impulse response of the filter can be described by the following equation:

$$y(n) = \sum_{i=1}^{n} x(i) \otimes h(n-i).$$

Those skilled in the art who have the benefit of this description will recognize that equation as a classical convolution equation. (2N−1) values of x and N values of y are required to determine n values of h. The corresponding set of convolution equations for sampling periods n . . . 2n−1 follows:

$$y_{2-1} = h_1 x_{2n-1} + h_2 x_{2n-2} + \dots + h_n x_n$$

$$y_{2n-2} = h_1 x_{2n-2} + h_2 x_{2n-3} + \dots + h_n x_{n-1} \dots$$

$$y_{2n-k} = h_1 x_{2n-k} + h_2 x_{2n-k-1} + \dots + h_n x_{n-k+1} \dots$$

$$y_n = h_1 x_n + h_2 x_{n-1} + \dots + h_n x_1$$

Here, n is the number of filter taps. The above equations can be written in a matrix form as follows:

$$\{Y\} = [X]\{H\} \Rightarrow \{H\} = [X]^{-1}\{Y\}$$

This invention includes using an inverse convolution for converting between the set of convolution equations and the matrix form equation above. This invention utilizes the inverse time domain convolution to back-calculate the coefficiency of the filter from the input and output signals using the filter equations.

In one example, a particular advantage is achieved by realizing that the matrix [X] takes the form of a symmetric Toeplitz matrix. This allows computing the inverse of that matrix more efficiently. Utilizing a symmetric Toeplitz matrix, reduces the computations required for obtaining the matrix inversion. Instead of requiring $n^3$ computations, the inversion can be accomplished utilizing on the order of $n^2$ computations. For example, using the inventive approach a 62 tap filter typically will require computations on the order of 3844, which are well within the capacity of most current digital signal processors for a given sampling frequency of an active noise cancellation system.

In one example, a 60 MHz processor with the application running at approximately 2 kHz, the number of clock cycles available are 30,000, which is sufficient for the above method to work. Because offline digital modeling is a background process, it will not affect the system adversely even if these computations take more than one algorithm cycle. A 123 tap (2*62−1) calculation will take less than 80 milliseconds, and averaging over 10 spectra will not cause a significant modeling time, assuming a zero percent overlap in spectral windows. The modeling time under such circumstances is still less than one second. As overlap increases, the modeling time may be decreased.

Solving the matrix inversion provides the values of the impulse response that are then used as the initial estimate of the model of the filter 34. This initial estimate may be used in combination with a least mean squares convergence algorithm to arrive at the desired filter value for actual noise cancellation.

In another example, multiple time domain response initial estimates of the digital model may be averaged over time. The average initial estimate is then used as part of the filter modeling.

In still another example, a plurality of initial estimates are determined and averaged to determine the filter value, thereby eliminating the convergence or least mean squares algorithm. Those skilled in the art who have the benefit of this description will realize which technique will provide the best results for determining the necessary digital filter values to meet the needs of their particular situation.

Utilizing a filter modeling technique according to this invention provides faster convergence or determination of the filter value and allows for using smaller or quieter modeling noises. The two-fold advantage of this invention simplifies the processing required during the modeling that occurs in an active noise cancellation system and allows for minimizing any noise recognition by an individual.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

I claim:

1. A method of determining a digital filter value for use in an active noise cancellation system that includes a speaker that generates the noise signal and a microphone that detects the noise signal, comprising the steps of:

applying a noise signal to the system;

determining a time domain response of the system to the noise signal, the time domain response including a plurality of speaker signals and a plurality of microphone signals;

using an inverse time domain convolution to obtain a symmetric Toeplitz matrix of the speaker signals;

estimating an initial filter value based upon the time domain response; and determining the filter value using the estimated initial filter value.

2. The method of claim 1, comprising adapting the filter value responsive to an error signal in the system by starting with the estimated initial filter value and converging to the determined filter value.

3. A method of determining a digital filter value for use in an active noise cancellation system, comprising the steps of:

applying a test signal to the system a plurality of times;

determining a time domain response of the system to each applied test signal;

estimating a plurality of non-zero initial filter values based upon the determined time domain responses, respectively; and determining an average estimated filter value by averaging the plurality of estimated non-zero initial filter values.

4. The method of claim 3, comprising determining the digital filter value as the average estimated filter value.

5. The method of claim 3, comprising using the average estimated filter value as an initial filter value in a converging process that results in the determined digital filter value.

6. A method of determining a digital filter value for use in a noise cancellation system that includes a speaker, a signal generator and a microphone, comprising the steps of:

determining a time domain response of the system to a test noise signal;

determining an initial non-zero estimate of the filter based upon the determined time domain response;

providing a signal from the signal generator to the speaker and the initial estimate of the filter;

combining a signal from the microphone with a signal from the filter that results from the signal generator providing an input to the initial estimate of the filter to thereby achieve a resulting error signal; and using the resulting error signal to update values of the filter.

7. The method of claim 6, comprising updating the values of the filter responsive to another error signal resulting from combining another signal from the microphone with a signal from the updated filter that results from the signal generator providing an input to the updated filter.

* * * * *